United States Patent [19]

Jessel, Jr. et al.

[11] Plant 4,623

[45] Jan. 13, 1981

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 37,573

[22] Filed: May 9, 1979

[51] Int. Cl.[3] ..... A01H 5/00

[52] U.S. Cl. ..... Plt./74

[58] Field of Search ..... Plt./74

*Primary Examiner*—Robert E. Bagwill
*Assistant Examiner*—James R. Feyrer
*Attorney, Agent, or Firm*—Donald D. Jeffery

[57] ABSTRACT

A chrysanthemum cultivar particularly characterized as to uniqueness by the combined characteristics of flat capitulum form; daisy capitulum type; medium lavender pink ray floret color with minimum color oxidation; yellow green (immature) to yellow (mature) disc floret color; diameter across face of capitulum ranging from 90 to 105 mm. at maturity; uniform nine week photoperiodic flowering response to short days; tall plant height when grown as a single stem cut spray; and semi-upright branching pattern.

7 Drawing Figures

The present invention comprises a new and distinct cultivar of *Chrysanthemum morifolium,* Ramat., herinafter referred to by the cultivar name Citation.

Citation is a product of a planned breeding program which had the objective of creating new chrysanthemum cultivars with daisy capitulum type, lavender pink ray floret color, nine week flowering response and with the ability to produce commercially acceptable quality in year round cut mum programs. Such traits in combination were not present in previously available commercial cultivars.

Citation was originated from a cross made in a controlled breeding program in Barberton, Ohio in 1975. The female parent was Accent (disclosed in U.S. Plant Pat. No. 3,945). The male parent of Citation was Gem (disclosed in U.S. Plant Pat. No. 3,740). Accent and Gem are products of the breeding program of the present inventors.

Citation was discovered and selected as one flowering plant within the progeny of the stated cross by Walter H. Jessel, Jr. and William E. Duffett on Nov. 10, 1976 in a controlled environment in Barberton, Ohio.

The first act of asexual reproduction of Citation was accomplished when vegetative cuttings were taken from the initial selection in January, 1977 in a controlled environment in Barberton, Ohio, by a technician working under formulations established and supervised by Walter H. Jessel, Jr. and William E. Duffett. Continued asexual reproduction by vegetative cuttings for evaluative tests in flowering and stock programs in conjunction with horticultural examination of selected plants initiated in November, 1977 has demonstrated that the combination of characteristics as herein disclosed for Citation are firmly fixed and are retained through successive generations of asexual reproduction.

Citation has not been observed under all possible environmental conditions. The phenotype may vary significantly with variations in environment such as temperature, light intensity, and day length. The following observations, measurements, and comparisons describe plants grown in Salinas, Calif. under greenhouse conditions which approximate those generally used in commercial practice.

The following traits have been repeatedly observed and are determined to be basic characteristics of Citation which in combination distinguish this chrysanthemum as a new and distinct cultivar:

(1) Flat capitulum form.

(2) Daisy capitulum type.

(3) Medium lavender pink ray floret color with minimum color oxidation.

(4) Yellow green (immature) to yellow (mature) disc floret color.

(5) Diameter across face of capitulum ranging from 90 to 105 mm. at maturity.

(6) Uniform nine week photoperiodic flowering response to short days.

(7) Tall plant height (attaining a height as a flowered plant of 80 to 105 cm. from a rooted cutting planted to short days from April through November flowerings).

(8) Semi-upright branching pattern.

The accompanying photographic drawings show typical inflorescence and foliage characteristics of Citation, with colors being as nearly true as possible with illustrations of this type.

Sheet 1 is a color photograph of Citation grown as a single stem cut spray.

Sheet 2 is a black and white photograph showing the foliage of Citation at three stages of growth.

Sheet 3 is a black and white photograph of the inflorescence of Citation.

Of the many commercial cultivars known to the present inventors, the most similar existing cultivars in comparison to Citation are Blue Marble (unpatented) and the parental cultivar Gem. Reference is made to attached Chart A which compares certain characteristics of Citation to those same characteristics of Blue Marble and Gem.

General comparisons are as follows:

(1) In comparison to Blue Marble, Citation has less oxidation of ray floret color, larger diameter across face of capitulum and taller plant height. The ray floret color, capitulum form, capitulum type, and flowering response of Citation are similar to those same characteristics of Blue Marble.

(2) In comparison to Gem, Citation has darker ray floret color, larger diameter across face of capitulum, taller plant height, and longer flowering response period. The capitulum form and capitulum type of Citation are similar to those same characteristics of Gem.

In the following description color references are made to A Limit Color Cascade by the Munsell Company, 1972 edition. The color values were determined between 3:30 and 4:00 p.m. on Mar. 9, 1979 under 100 foot-candle light intensity at Salinas, Calif.

Classification:

*Botanical.*—*Chrysanthemum morifolium,* Ramat., cv Citation.

*Commercial.*—Cut daisy spray.

I. Inflorescence:

A. *Capitulum.*—Form: Flat. Type: Daisy. Diameter across face: 90–105 mm.

B. *Corolla of ray florets.*— General tonality: Medium lavender pink, approximately 45-3. Color (abaxial): Ranging from 45-6 to 45-5 (immature) and from 46-4 streaked over 45-4 to 45-3 streaked over 46-2. Color (adaxial): Approximately 46-4 streaked over 46-2.

C. *Corolla of disc florets.*—Color (abaxial): 26-6. Color (adaxial): Ranging from 25-14 to approximately 22-9 (immature) to 26-6 (mature).

D. *Reproductive organs.*—Gynoecium: Present both ray and disc florets. Androecium: Present disc florets only; numerous; moderate to scant pollen.

II. Plant:

A. *General appearance.*—Height: Tall, attaining a height of 70 to 75 cm. as a flowered plant from a rooted cutting with no long days for April through November flowerings. Branching pattern: Semi-upright.

B. *Foliage.*—Color (abaxial): Approximately 21-15. Color (adaxial): Approximately 21-14 overlaid with white. Shape: Deeply lobed and moderately serrated.

CHART A

COMPARISON OF CITATION, BLUE MARBLE AND GEM

| CULTIVAR | RAY FLORET COLOR | CAPITULUM FORM & TYPE | DIAMETER ACROSS FACE OF CAPITULUM |
|---|---|---|---|
| Citation | Medium lavender pink with minimum color oxidation | Flat Daisy | 90 to 105 mm. |
| Blue Marble | Medium lavender pink with rapid color oxidation | Flat Daisy | 60 to 85 mm. |
| Gem | Light lavender pink with minimum color oxidation | Flat Daisy | 70 to 85 mm. |

| CULTIVAR | PLANT HEIGHT | FLOWERING RESPONSE PERIOD |
|---|---|---|
| Citation | Tall 70 to 75 cm. | 9 week |
| Blue Marble | Medium, 60 to 65 cm. | 9 week |
| Gem | Short 50 to 55 cm. | 7 week |

COMPARISONS MADE OF PLANTS GROWN AS SINGLE STEM CUT SPRAYS WITH NO LONG DAYS IN SALINAS, CALIFORNIA FOR APRIL THROUGH NOVEMBER FLOWERINGS.

We claim:

1. A new and distinct cultivar *Chrysanthemum morifolium,* Ramat., plant known by the cultivar name Citation, as described and illustrated, and particularly characterized as to uniqueness by the combined characteristics of flat capitulum form; daisy capitulum type; medium lavender pink ray floret color with minimum color oxidation; yellow green (immature) to yellow (mature) disc floret color; diameter across face of capitulum ranging from 90 to 105 mm. at maturity; uniform nine week photoperiodic flowering response to short days; tall plant height when grown as a single stem cut spray; and semi-upright branching pattern.

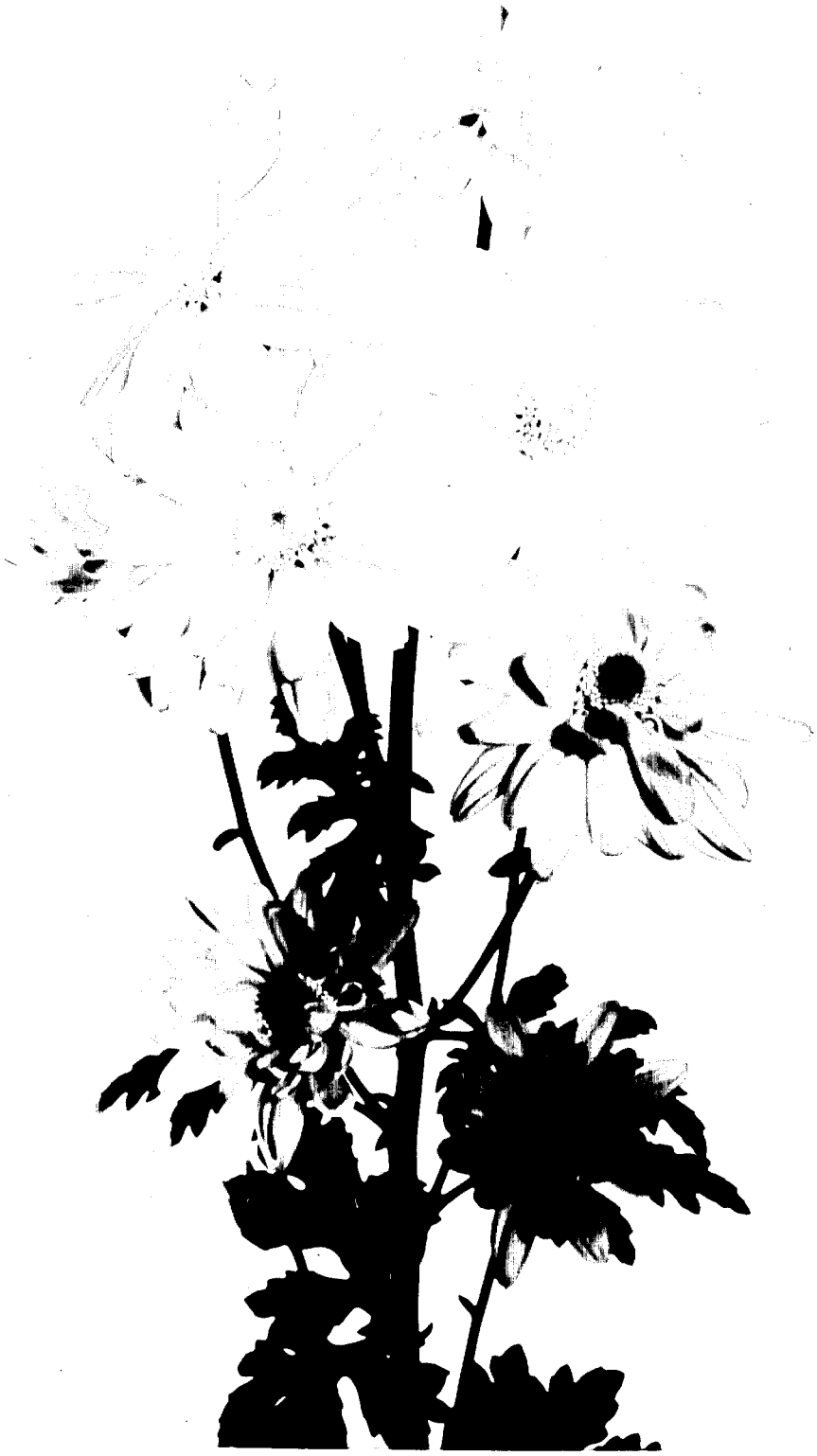

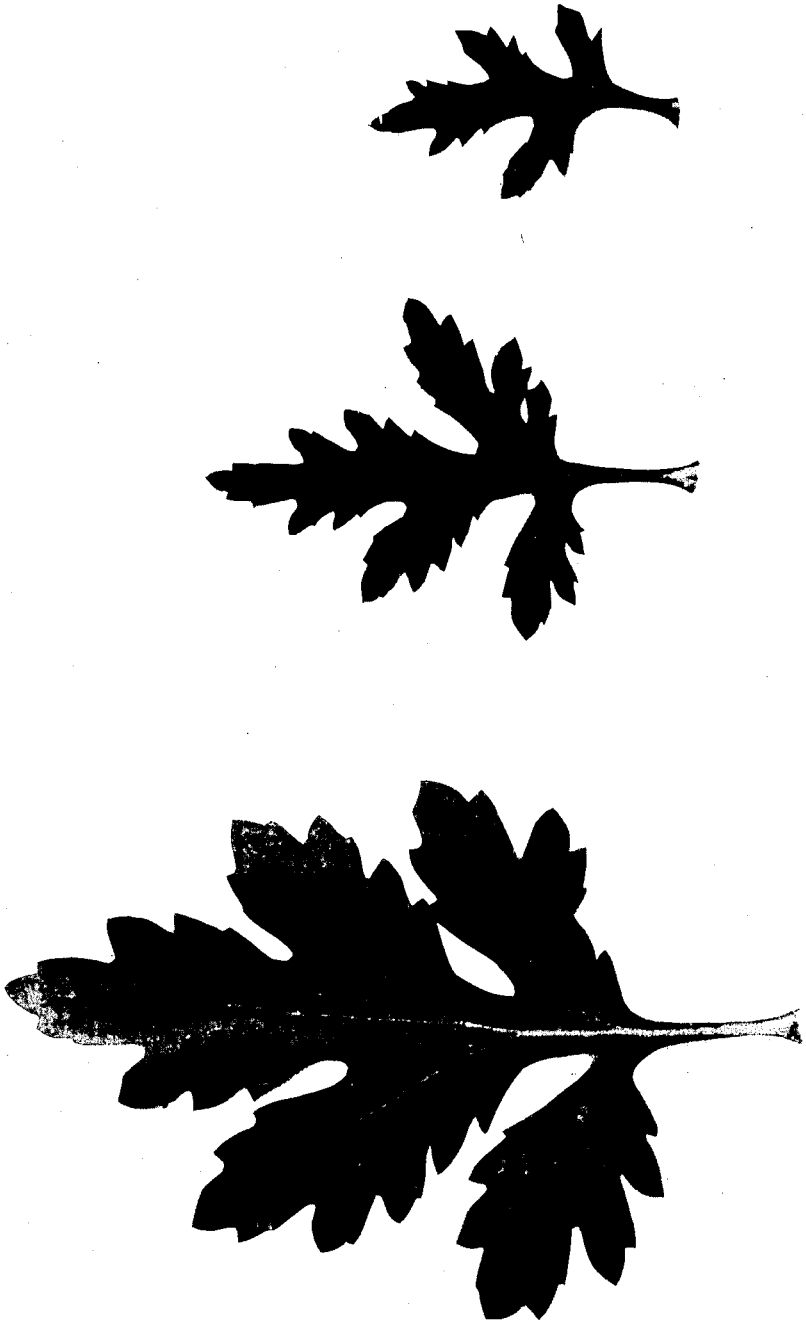

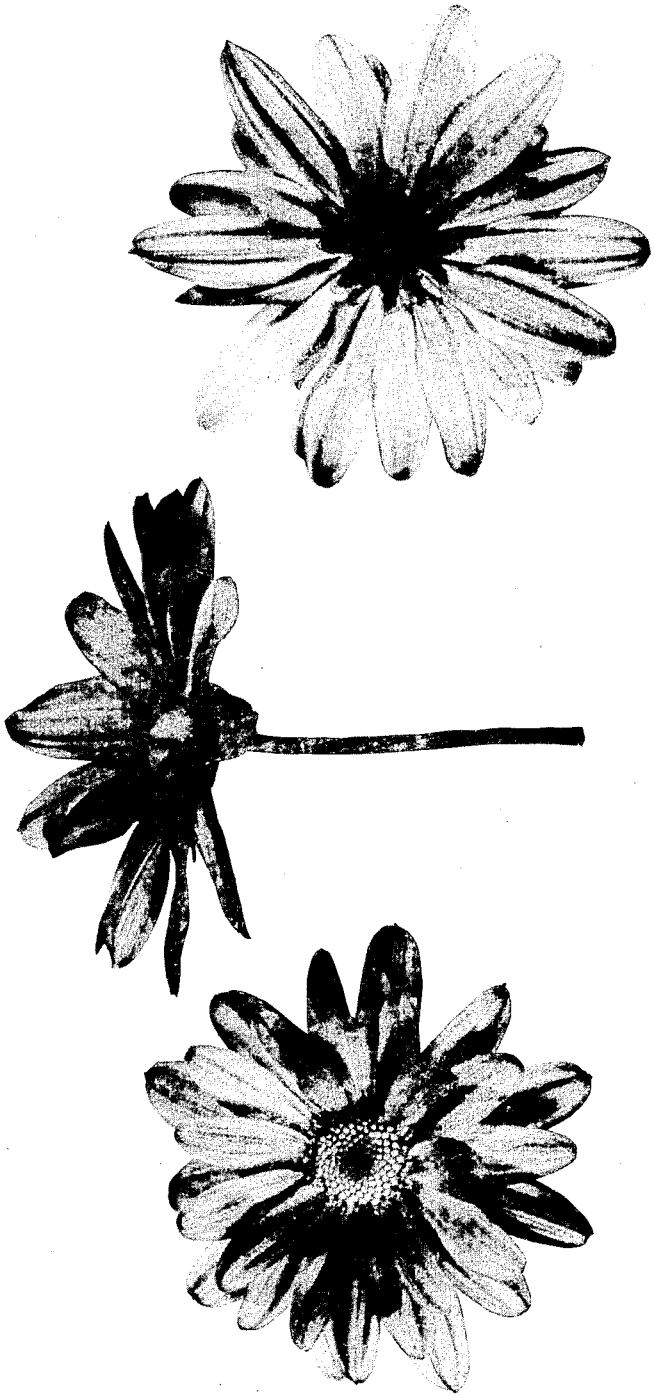

* * * * *